(12) United States Patent
Kok et al.

(10) Patent No.: US 12,121,324 B2
(45) Date of Patent: Oct. 22, 2024

(54) ANIMAL DETECTION

(71) Applicant: CAUCUS CONNECT LIMITED, Birmingham (GB)

(72) Inventors: Terence Kok, Birmingham (GB); Mathew V. Kaye, Birmingham (GB)

(73) Assignee: Caucus Connect Limited (GB)

( * ) Notice: Subject to any disclaimer, the term of this patent is extended or adjusted under 35 U.S.C. 154(b) by 0 days.

(21) Appl. No.: 17/767,877

(22) PCT Filed: Oct. 12, 2020

(86) PCT No.: PCT/IB2020/059554
§ 371 (c)(1),
(2) Date: Apr. 8, 2022

(87) PCT Pub. No.: WO2021/070153
PCT Pub. Date: Apr. 15, 2021

(65) Prior Publication Data
US 2024/0081652 A1    Mar. 14, 2024

(30) Foreign Application Priority Data

Oct. 11, 2019   (GB) ...................................... 1914775

(51) Int. Cl.
*A61B 5/01*     (2006.01)
*A01M 31/00*    (2006.01)
*G06N 20/00*    (2019.01)
*G06T 7/70*     (2017.01)

(52) U.S. Cl.
CPC ............. *A61B 5/01* (2013.01); *A01M 31/002* (2013.01); *G06N 20/00* (2019.01); *G06T 7/70* (2017.01); *G06T 2207/10048* (2013.01)

(58) Field of Classification Search
CPC ....... A61B 5/01; A01M 31/002; G06N 20/00; G06T 7/70; G06T 2207/10048
See application file for complete search history.

(56) References Cited

U.S. PATENT DOCUMENTS

| 11,666,216 B2* | 6/2023 | Scherer | ................... H04B 5/24 600/347 |
| 2007/0230744 A1 | 10/2007 | Dronge | |
| 2010/0214408 A1 | 8/2010 | McClure et al. | |
| 2013/0319336 A1* | 12/2013 | Thompson | ........... A01K 29/005 119/14.02 |
| 2014/0279600 A1 | 9/2014 | Chait | |
| 2015/0049941 A1* | 2/2015 | Hall | ........................ G01J 3/463 382/165 |
| 2015/0302241 A1* | 10/2015 | Eineren | .................. G06V 40/10 382/110 |

(Continued)

FOREIGN PATENT DOCUMENTS

| JP | 2017532041 A | 11/2017 |
| WO | 15/139091 A1 | 9/2015 |
| WO | 17/120189 A1 | 7/2017 |

*Primary Examiner* — Mohamed Barakat
(74) *Attorney, Agent, or Firm* — Fishman Stewart PLLC

(57) ABSTRACT

A detection apparatus for identifying the presence of a target warm blooded animal in a detection zone and a method of detecting a warm-blooded animal are disclosed. The detection apparatus utilizes a thermal imaging camera, a sensor, and a microcontroller to capture data on an array and interpret data, and a signaller for sending data indicating the presence of a target animal.

20 Claims, 4 Drawing Sheets

(56) References Cited

U.S. PATENT DOCUMENTS

| | | |
|---|---|---|
| 2016/0277688 A1 | 9/2016 | Gaskamp et al. |
| 2018/0177178 A1 | 6/2018 | Bhakta et al. |
| 2019/0159681 A1* | 5/2019 | Sugaya .................. G06V 20/52 |
| 2019/0166823 A1 | 6/2019 | Dick |
| 2021/0378231 A1 | 12/2021 | Howard et al. |
| 2022/0039357 A1* | 2/2022 | Roth .................... A01K 29/005 |

* cited by examiner

ANIMAL DETECTION

CROSS-REFERENCE TO RELATED APPLICATION

This application claims priority to International Patent Application No. PCT/IB2020/059554 filed on Oct. 12, 2020, which also claims priority to Great Britain Patent Application No. GB 1914775.0 filed on Oct. 11, 2019, the contents of each of which is hereby incorporated reference in their entirety.

TECHNICAL FIELD

This invention relates to the detection of warm-blooded animals. More particularly it relates to the detection of mammals, particularly, but not exclusively pests such as rodents.

BACKGROUND

The pest control industry uses a variety of sensor technologies to detect pests. These are not particularly discriminatory (can't identify particular pests) and are prone to false positive reporting, which makes them expensive to operate as personnel make site visits based on inaccurate data.

Also, because they provide little, if any, e.g. behavioural information, addressing the causative problem is not possible.

Prior art identified includes:
US2010/214408, which relates to an image processing sensor system for capturing and processing images;
US2007/230744, which relates to a security system including motion detectors connected to cameras;
WO2015/139091, which relates to a system for detecting target animals in a protected area; and
US2018/177178, which is an animal deterrent apparatus.

The present invention seeks to collect and report information in real time, providing data which is more insightful, thereby allowing more efficient management of pests, such as rats.

It also relates to the management of data and battery life such that apparatus can be placed in field situations were access to electricity and WIFI may be limited.

SUMMARY

Broadly there is provided a detection apparatus, for identifying the presence of a target warm blooded animal in a detection zone, comprises:
i) a sensor which when triggered wakes up a microcontroller unit (MCU) powered by a battery;
ii) a thermal imaging camera, positioned so as to detect the warm-blooded animal in the detection zone;
iii) a means for capturing temperature and location and displaying it as a plurality of co-ordinates on an array;
iv) a computing means which interrogates at least one of temperature intensity and a location area, and based on an algorithm records or rejects an indicator signal with an associated location; and
v) a signaller for sending data indicating the presence of a target animal.

In accordance with a first aspect of the present inventions there is provided a detection apparatus (10), for identifying the presence of a target warm blooded animal (300) in a detection zone (20), comprises:

i) a sensor (30) which when triggered wakes (42) up a microcontroller unit (MCU) (40) powered by a battery (150);
ii) a thermal imaging camera (50), positioned so as to detect the warm blooded animal (300) in the detection zone (20);
iii) a means (50) for capturing temperature (70) and location (80) and displaying it as a plurality of co-ordinates (90) on an array (100);
iv) a computing means (110) which interrogates at least one of temperature intensity (72) and a location area (82), and based on an algorithm (112) and machine learning records (120) or rejects (130) an indicator signal (140) with an associated location (80) and stores data simply as a product which correlates to a simple quantitative or qualitative figure, such as, a simple numerical value associated with a co-ordinate; and
v) a signaller (190) for sending data (180) indicating the presence of a target animal (300).

Preferably if the computing means determines the signal was not a target warm-blooded animal it sends the MCU back into a sleep mode, preserving a battery's power.

If the computing means determines the signal was likely a target warm-blooded animal, it determines, within a pre-determined time, whether the animal moves and, in the event a pre-determined time passes without further movement, sends the MCU back into a sleep mode. Alternatively, if additional movement is detected within the pre-determined time it sends data, via the signaller, indicating the presence of a target animal.

Preferably the detection apparatus can discriminate animal size allowing it to determine it is a target animal.

Preferably the detection apparatus can determine direction of travel of an animal.

For rodents it is preferred that the thermal imaging camera is positioned above the detection zone, although other configurations are possible.

Preferably the thermal imaging camera has a field of view of at least 90 degrees and more preferably has a field of view of about 110 degrees.

By varying the height of the thermal imaging camera above the detection zone it is possible to increase or decrease the area being monitored.

For a camera with a 110-degree field of view the following relationship exists—Table 1.

| HEIGHT (M) | AREA COVERAGE (M$^2$) |
|---|---|
| 0.30 | 0.58 |
| 0.40 | 1.03 |
| 0.50 | 1.60 |
| 0.60 | 2.31 |
| 0.70 | 3.14 |
| 0.80 | 4.10 |
| 0.90 | 5.19 |
| 1.00 | 6.41 |

Preferably the signaller is configured to send data in real time.

Most preferably the detection apparatus is integrated into an internet enabled pest control management system.

The components of the apparatus including a battery, microcontroller and signaller are releasably sealed in a housing with respectively a thermal imaging camera, motion activated sensor and distance sensor, for auto-calibrating the height from the detection zone, being disposed through one face of the housing.

The distance sensor is used to auto calibrate a vertical distance between the thermal imaging camera and a point on the detection zone.

Broadly there is provided a method of detecting a warm-blooded animal comprising the steps of:
 i) Setting up a detection apparatus above a detection zone;
 ii) Detecting the presence of the animal using a motion sensor which triggers the waking of a microcontroller unit (MCU);
 iii) Using a thermal imaging camera to identify the presence of the animal and using temperature and location sensing to identify a target animal and optionally its direction of travel; and
 iv) Based on data captured send data, via a signaller, to a user to inform the user of the presence of the target animal.

According to a second aspect of the present invention there is provided a method of detecting a warm-blooded animal comprising the steps of:
 i) Setting up a detection apparatus (10) above a detection zone (20);
 ii) Detecting the presence of the animal using a motion sensor which triggers the waking (42) of a microcontroller unit (MCU) (40);
 iii) Using a thermal imaging camera (50) to identify the presence of the animal and using temperature (70) and location (80) sensing to identify a target animal; and
 iv) Based on data captured send data (180), via a signaller (190), to a user to inform the user of the presence of the target animal wherein the apparatus utilises a means (50) for capturing temperature (70) and location (80) and displays it as a plurality of co-ordinates (90) on an array (100); interrogates at least one of temperature intensity (72) and location area (82) and based on an algorithm (112) and machine learning records (120) or rejects (130) a signal (140) with an associated location (80) and stores data simply as a product which correlates to a simple quantitative or qualitative figure, such as, a simple numerical value associated with a co-ordinate.

Preferably the method uses a sensor to calibrate the apparatus by determining the distance between the thermal imaging camera and the point on the detection zone.

The method further utilises a motion sensor to turn on the microprocessor unit to control battery life.

The method utilises a means for capturing temperature and location and displays it as a plurality of co-ordinates on an array; interrogates at least one of temperature intensity and location area and based on an algorithm records or rejects a signal and an associated location.

The use of an algorithm, and machine learning, to integrate and interpret temperature and location data and store data simply as a product which correlates to a simple quantitative or qualitative figure (such as a simple numerical value) associated with a co-ordinate enables the data stored and/or transmitted to be of a compact nature such that battery life can be massively enhanced from a few months to several years.

Preferably power is manages following a protocol as substantially illustrated in FIG. 5.

BRIEF DESCRIPTION OF THE DRAWINGS

Embodiments of the invention are further described hereinafter with reference to the accompanying drawings, in which.

DETAILED DESCRIPTION

Figure 1:
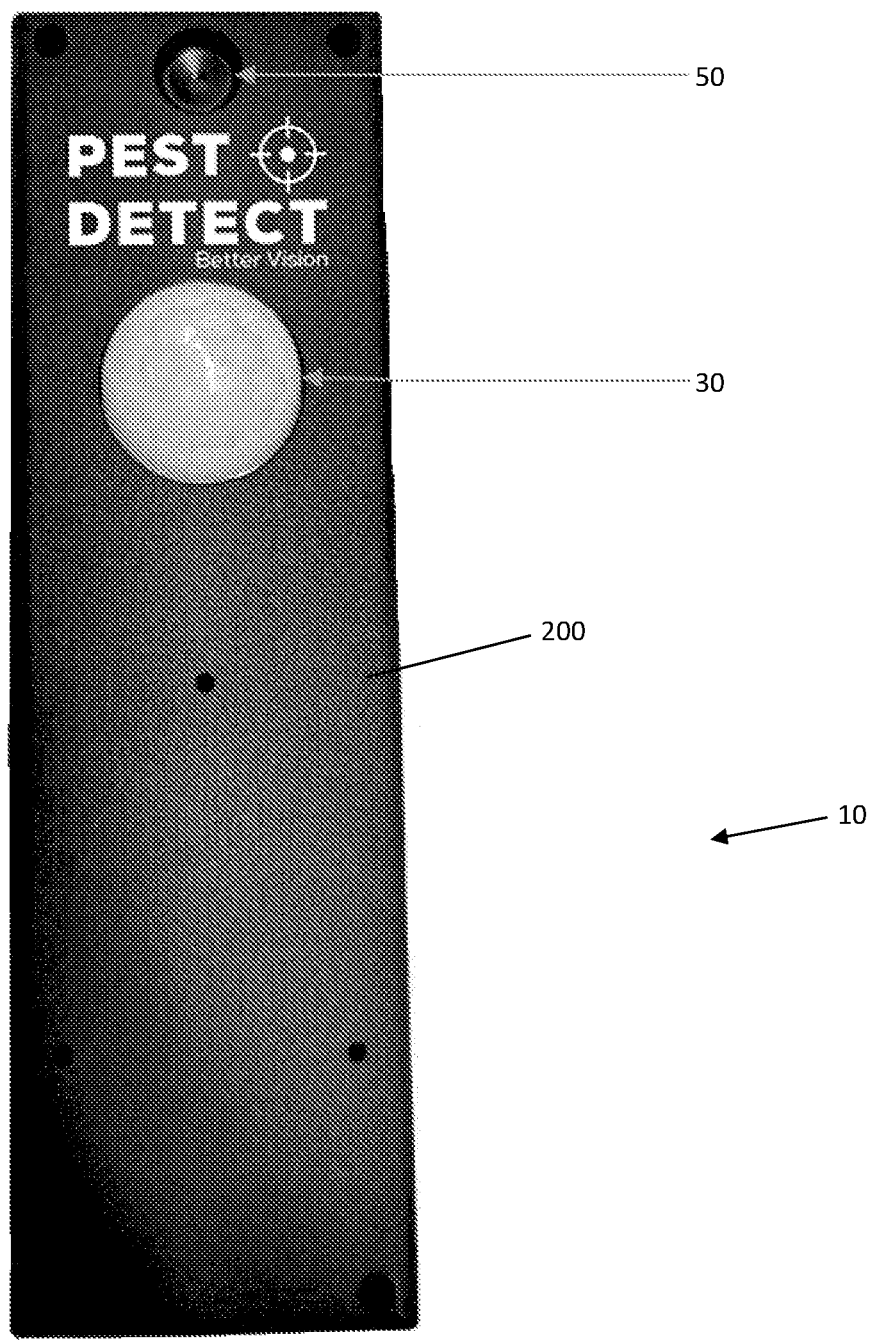
FIG. 1 is an apparatus of one embodiment of the invention.

FIG. 1 is an illustration of one embodiment of apparatus (10) of the invention. It comprises a housing (200) inside of which are housed a plurality of components, as described further with reference to FIG. 2. Projecting out from the housing are at least a thermal imaging camera (50) and a motion sensor (30). Preferably the apparatus also includes a sensor (60) for auto calibrating the height of the apparatus above a detection zone (20) as illustrated in FIG. 3.

Figure 2:
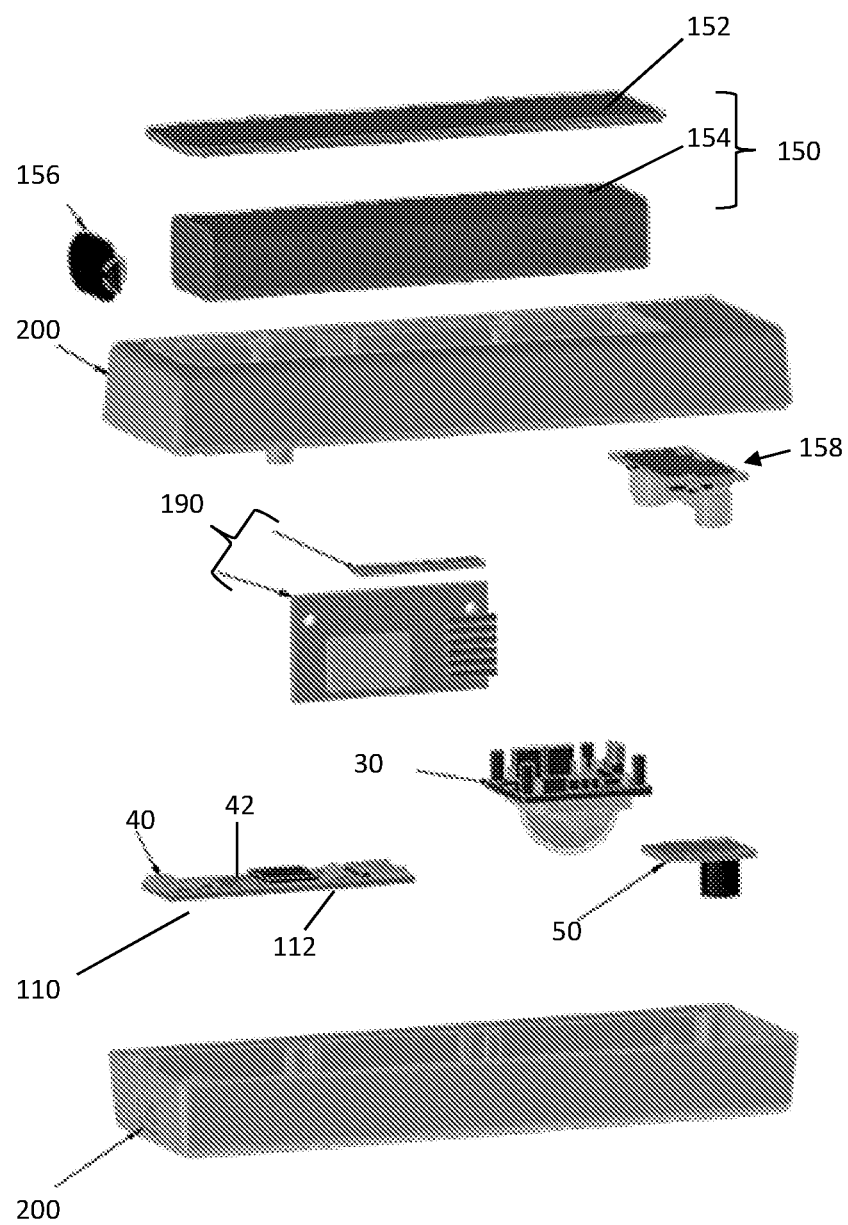
FIG. 2 is a simplified exploded view of an apparatus of the invention.

As shown in FIG. 2 the housing (200) comprises two plastic mouldings which connect to one another. A thermal imaging camera (50) and PIR sensor (30), as well as an ultrasonic sensor for autocalibration of height (not shown), are mounted through a face in the housing.

Figure 5:
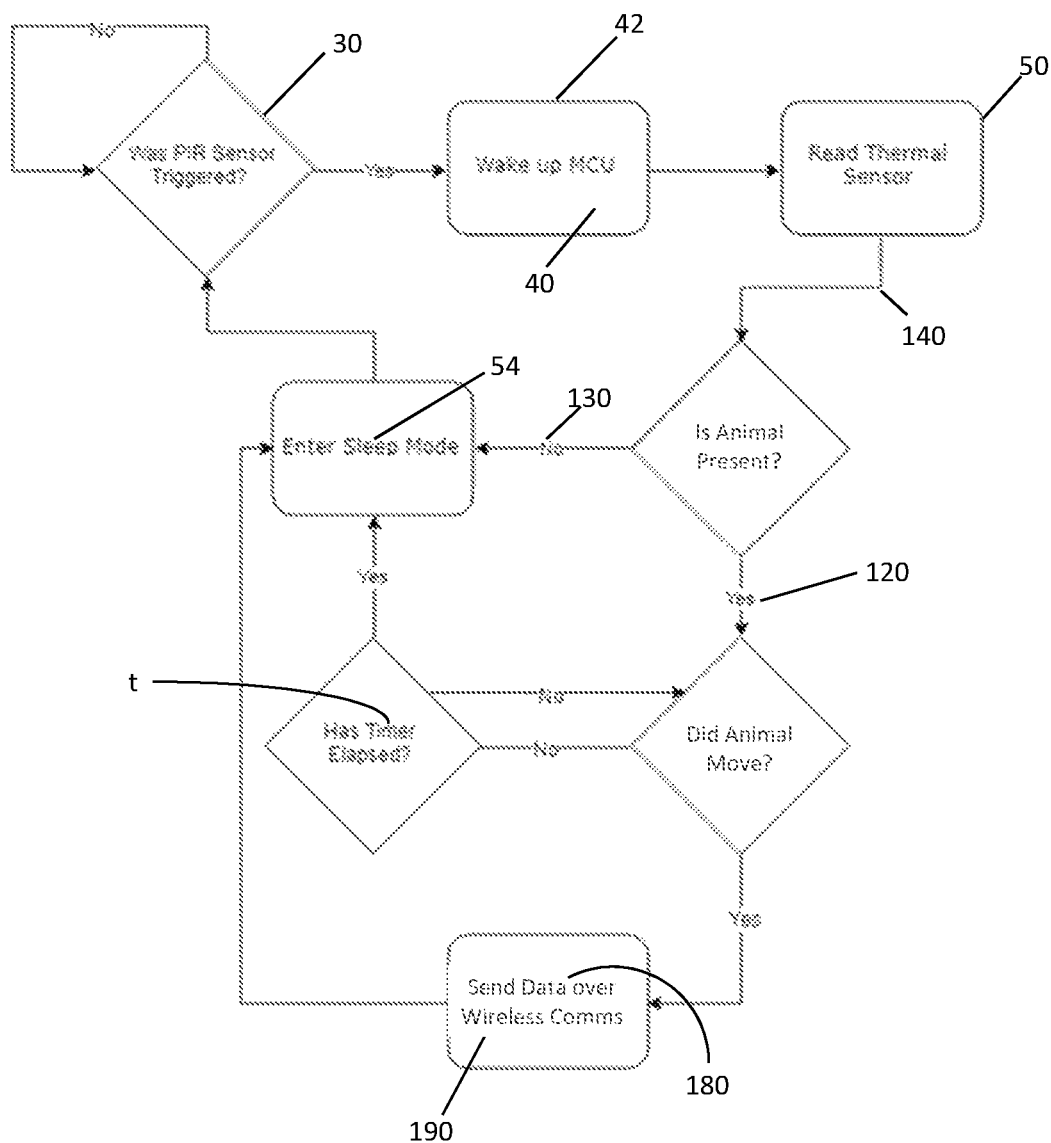
FIG. 5 is a flow diagram illustrating a preferred operational methodology.

Fitted within the housing, are a microcontroller unit (MCU) (40), battery (150), in a separate case (152, 154) along with a connector (156). The power is managed using a power regulator (158) and a signaller (190) manages the sending of data based on e.g. a protocol as illustrated in FIG. 5.

Figure 3:
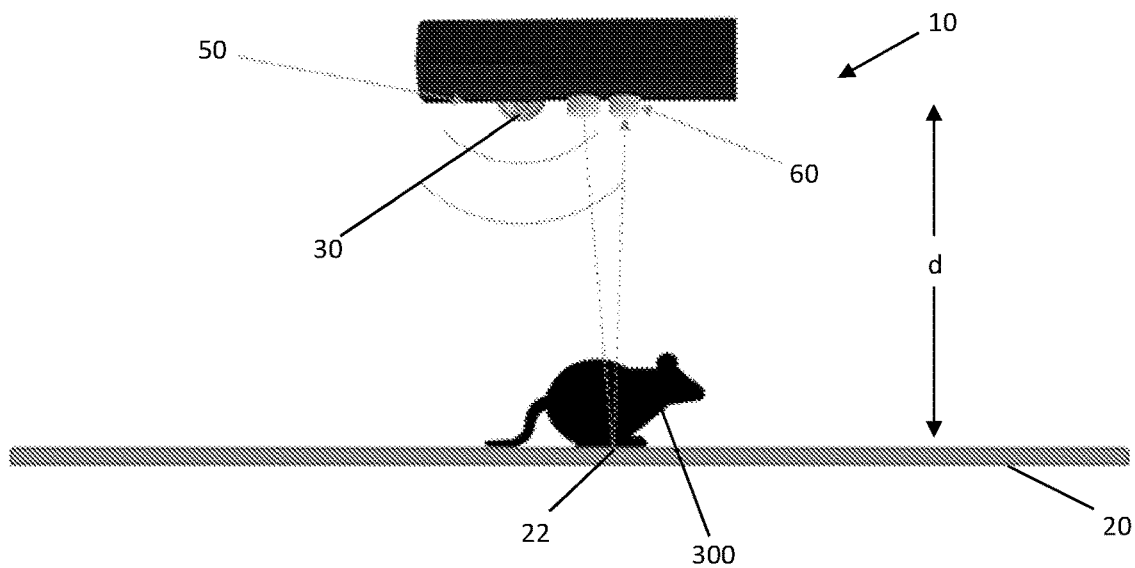
FIG. 3 is an apparatus of the invention in use.

As illustrated in FIG. 3 the apparatus (10) is positioned a distance (d) above a point (22) on the detection zone (20). An ultrasonic, or other, sensor (60) may be used to provide for autocalibration as the sensitivity and range of detection is dependent upon the distance from the ground and field of view of the thermal imaging camera.

Figure 4:
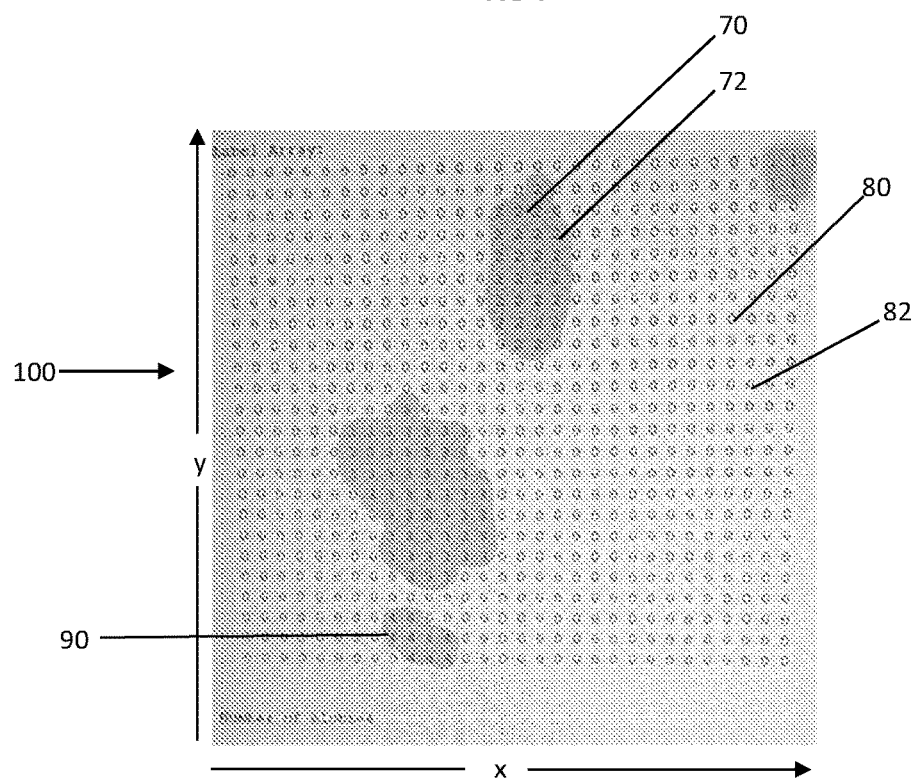
FIG. 4 is array showing heat detection.

If a rodent (300) enters the detection zone it triggers a motion sensor (30) which once triggered wakes (42) a microcontroller (40). The thermal sensor (50) detects the rodent and captures thermal image data including temperature (70) and intensity (72) at a location (80) or location area (82) which are captured as an array (100)—FIG. 4 capturing the data as co-ordinates (90). An algorithm interprets this data which can be used to identify whether the data is consistent with a target animal or not and depending on the conclusion can send the device back to sleep (54) or continue to monitor and send data (180), including animal size or it's direction of movement via signaller (190) wirelessly. The apparatus has a clock (not shown) enabling date and time data to be monitored as well as being able to determine time periods (t), which can be used in the management of the detection and power management process.

The invention claimed is:

1. A detection apparatus, for identifying the presence of a target warm blooded animal in a detection zone, comprises:
 i) a sensor that when triggered wakes up a microcontroller unit (MCU) powered by a battery;
 ii) a thermal imaging camera, positioned so as to detect the warm blooded animal in the detection zone;
 iii) a thermal sensor that captures temperature and location and displays the temperature and location as a plurality of co-ordinates on an array;
 iv) a computer that interrogates at least one of a temperature intensity and a location area, and based on an algorithm and machine learning records or rejects an indicator signal with an associated location and stores data simply as a product which correlates to a simple quantitative or qualitative figure including a simple numerical value associated with a co-ordinate; and v) a signaller for sending data indicating the presence of the target animal.

2. The detection apparatus as claimed in claim 1, wherein the data further indicates animal size of the target animal.

3. The detection apparatus as claimed in claim 1, wherein the data further indicates a direction of travel of the target animal.

4. The detection apparatus as claimed in claim 1, wherein the thermal imaging camera is positioned above the detection zone.

5. The detection apparatus as claimed in claim 1, wherein the thermal imaging camera has a field of view of at least 90 degrees.

6. The detection apparatus as claimed in claim 5, wherein the thermal imaging camera has a field of view of about 110 degrees.

7. The detection apparatus as claimed in claim 1, wherein the signaller is configured to send data in real time.

8. The detection apparatus as claimed in claim 1, which is integrated into an internet enabled pest control management system.

9. The detection apparatus as claimed in claim 1, further comprising a housing that seals the battery, the MCU and the signaller.

10. The detection apparatus as claimed in claim 1, further comprising a distance sensor for calibrating a vertical distance between the thermal imaging camera and a point on the detection zone.

11. A method of detecting a warm-blooded animal comprising the steps of:

i) setting up a detection apparatus above a detection zone;

ii) detecting the presence of the animal using a motion sensor that triggers a waking of a microcontroller unit (MCU);

iii) using a thermal imaging camera to identify the presence of the animal and using temperature and location sensing to identify a target animal; and iv) based on data captured sending data, via a signaller, to a user to inform the user of the presence of the target animal;

wherein the detection apparatus utilises a thermal sensor that captures temperature and location and displays the temperature and location as a plurality of co-ordinates on an array; interrogates at least one of temperature intensity and location area and based on an algorithm and machine learning records or rejects a signal with an associated location and stores data simply as a product which correlates to a simple quantitative or qualitative figure including a simple numerical value associated with a co-ordinate.

12. The method as claimed in claim 11, further comprising using a sensor to calibrate the detection apparatus with respect to a distance between the thermal imaging camera and a point on the detection zone.

13. The method as claimed in claim 11, wherein a motion sensor is used to turn on the MCU to control battery life.

14. The method as claimed in claim 11, wherein the signaller manages the sending of data based on whether the target animal is present and whether the target animal has moved.

15. The method as claimed in claim 14, wherein the signaller is configured to send data in real time.

16. The method as claimed in claim 11, wherein the detection apparatus is configured to discriminate animal size.

17. The method as claimed in claim 11, wherein the detection apparatus is configured to determine direction of travel of the animal.

18. The method as claimed in claim 11, wherein the thermal imaging camera has a field of view of at least 90 degrees.

19. The method as claimed in claim 18, wherein the thermal imaging camera is positioned above the detection zone.

20. The method as claimed in claim 11, further comprising calibrating via a distance sensor a vertical distance between the thermal imaging camera and a point on the detection zone.

* * * * *